United States Patent
Okamoto et al.

(10) Patent No.: US 9,932,282 B2
(45) Date of Patent: Apr. 3, 2018

(54) METHOD FOR PRODUCING TRANS-1-CHLORO-3,3,3-TRIFLUORO-PROPENE

(71) Applicant: Central Glass Company, Limited, Yamaguchi (JP)

(72) Inventors: Satoru Okamoto, Saitama (JP); Fuyuhiko Sakyu, Tokyo (JP); Masatomi Kanai, Saitama (JP); Takamasa Kitamoto, Saitama (JP)

(73) Assignee: CENTRAL GLASS COMPANY, LIMITED, Yamaguchi (JP)

( * ) Notice: Subject to any disclaimer, the term of this patent is extended or adjusted under 35 U.S.C. 154(b) by 0 days.

(21) Appl. No.: 15/400,607

(22) Filed: Jan. 6, 2017

(65) Prior Publication Data
US 2017/0113986 A1    Apr. 27, 2017

Related U.S. Application Data

(63) Continuation of application No. PCT/JP2015/069784, filed on Jul. 9, 2015.

(30) Foreign Application Priority Data

Jul. 15, 2014  (JP) .................. 2014-145033

(51) Int. Cl.
*C07C 17/25* (2006.01)
*C07C 17/20* (2006.01)

(52) U.S. Cl.
CPC ............ *C07C 17/25* (2013.01); *C07C 17/206* (2013.01)

(58) Field of Classification Search
CPC ..... C07C 17/206; C07C 17/25; C07C 17/358; C07C 17/383; C07C 21/18; C01B 7/0712
See application file for complete search history.

(56) References Cited

U.S. PATENT DOCUMENTS

| | | | | |
|---|---|---|---|---|
| 5,811,603 | A | * | 9/1998 | Elsheikh .................. C07C 17/00 570/166 |
| 6,472,573 | B1 | * | 10/2002 | Yamamoto .............. C07C 17/38 570/164 |
| 2005/0033097 | A1 | | 2/2005 | Tung et al. |
| 2012/0059199 | A1 | * | 3/2012 | Pokrovski ............. C01B 7/0706 570/155 |
| 2012/0059200 | A1 | | 3/2012 | Pokrovski et al. |
| 2014/0171698 | A1 | | 6/2014 | Elsheikh et al. |
| 2014/0336424 | A1 | | 11/2014 | Okamoto et al. |
| 2015/0011806 | A1 | | 1/2015 | Hibino et al. |
| 2015/0099907 | A1 | * | 4/2015 | Imura ................... C07C 17/358 570/151 |
| 2015/0203424 | A1 | | 7/2015 | Okamoto et al. |

FOREIGN PATENT DOCUMENTS

| | | |
|---|---|---|
| EP | 877009 A1 | 11/1998 |
| EP | 939071 A1 | 9/1999 |
| EP | 2341040 A1 | 7/2011 |
| JP | H09-183740 A | 7/1997 |
| JP | H11-180908 A | 7/1999 |
| JP | 2000-7591 A | 1/2000 |
| JP | 2000-7592 A | 1/2000 |
| JP | 2007-501843 A | 2/2007 |
| JP | 2013-107848 A | 6/2013 |
| JP | 2013-520421 A | 6/2013 |
| JP | 2013-139414 A | 7/2013 |
| JP | 2013-538809 A | 10/2013 |
| JP | 2014-051485 A | 3/2014 |
| WO | 2011/103035 A2 | 8/2011 |
| WO | 2012/030797 A2 | 3/2012 |

OTHER PUBLICATIONS

English Translation of Written Opinion of the International Searching Authority dated October 6, 2015 for PCT Application No. PCT/JP2015/069784.
International Search Report dated Oct. 6, 2015 for International Application No. PCT/JP2015/069784.
Written Opinion of the International Searching Authority dated Oct. 6, 2015 for International Application No. PCT/JP2015/069784.
European Office Action dated Nov. 22, 2017 for corresponding European Application No. 15822146.5.

* cited by examiner

*Primary Examiner* — Jafar Parsa
(74) *Attorney, Agent, or Firm* — Hauptman Ham, LLP

(57) ABSTRACT

A method for producing 1-chloro-3,3,3-trifluoropropene efficiently from an intermediate product having a low reactivity is provided. A method for producing trans-1-chloro-3,3,3-trifluoropropene comprising reacting a halogenated hydrocarbon compound having 3 carbon atoms represented by Formula (1) shown below in a gas phase with hydrogen fluoride in the presence of chlorine is provided. $C_3H_XCl_YF_Z$ (1) wherein X is 2 or 3; and when X=2, Y is an integer from 1 to 4, Z is an integer from 0 to 3, and Y+Z=4; and when X=3, Y is an integer from 1 to 5, Z is an integer from 0 to 4, and Y+Z=5; provided that Formula (1) shown above represents a halogenated hydrocarbon compound having 3 carbon atoms excluding trans-1-chloro-3,3,3-trifluoropropene.

20 Claims, 1 Drawing Sheet

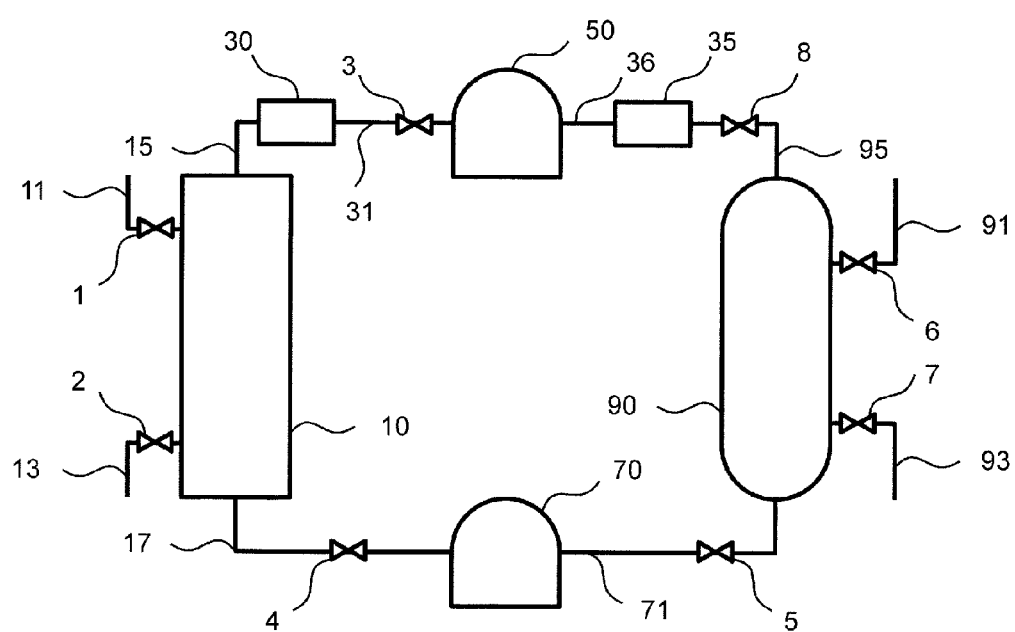

METHOD FOR PRODUCING TRANS-1-CHLORO-3,3,3-TRIFLUOROPROPENE

CROSS REFERENCE TO RELATED APPLICATIONS

This application is based upon and claims the benefit of priority from the prior Japanese Patent Application No. 2014-145033, filed on Jul. 15, 2014, and PCT Application No. PCT/JP2015/069784, filed on Jul. 9, 2015 and the entire contents of which are incorporated herein by reference.

FIELD

The present invention relates to a method for producing trans-1-chloro-3,3,3-trifluoropropene from a halogenated hydrocarbon compound having 3 carbon atoms.

BACKGROUND

The trans-1-chloro-3,3,3-trifluoropropene (abbreviated designation: 1233zd(E)) is a compound useful as a next-generation polyurethane foaming agent, working fluid, refrigerant and the like which have low global warming potentials (GWP).

Usually, 1-chloro-3,3,3-trifluoropropene (abbreviated designation: 1233zd) is produced using a fluorinating catalyst by fluorinating 1,1,1,3,3-pentachloropropane (abbreviated designation: 240fa) with hydrogen fluoride or by fluorinating 1,1,3,3-tetrachloro-2-propene (abbreviated designation: 1230za) with hydrogen fluoride. This fluorination is conducted as a gas-phase or liquid-phase reaction, and the liquid-phase reaction is conducted under pressure.

For example, Japanese Patent Application Laid-Open No. H9-183740 describes a method for obtaining 1-chloro-3,3,3-trifluoropropene (1233zd) by reacting 1,1,1,3,3-pentachloropropane (240fa) with hydrogen fluoride in the presence of a fluorinating solid catalyst in a gas phase. Japanese Patent Application Laid-Open No. H11-180908 describes a method for obtaining 1-chloro-3,3,3-trifluoropropene (1233zd) by a catalyst-free reaction of 1,1,1,3,3-pentachloropropane (240fa) with hydrogen fluoride. Japanese Unexamined Patent Application Publication (Translation of PCT Application) No. 2007-501843 describes a method for producing 1-chloro-3,3,3-trifluoropropene (1233zd) by reaction of 1,1,1,3,3-pentachloropropane (240fa) in a reaction vessel in the presence of Lewis acid catalyst or Lewis acid catalyst mixture at a temperature below 150° C. in a liquid phase, continuous recovery of hydrogen chloride and 1-chloro-3,3,3-trifluoropropene (1233zd) generated in the reaction vessel, and isolation of 1-chloro-3,3,3-trifluoropropene (1233zd) obtained in the previous step.

When reacting 1,1,1,3,3-pentachloropropane (240fa) with hydrogen fluoride to obtain 1-chloro-3,3,3-trifluoropropene (1233zd), an equilibrated reaction under the influence of the partial pressures of hydrogen fluoride and hydrogen chloride is established, and the reaction product contains, in addition to 1-chloro-3,3,3-trifluoropropene (1233zd), a more intensively fluorinated product such as 1,1,1,3,3-pentafluoropropane (abbreviated designation: 245fa) and the like, or a product having a lower fluorination degree such as 1,1,3,3-tetrachloro-1-fluoropropane (abbreviated designation: 241fa), 1,3,3-trichloro-1,1-difluoropropane (abbreviated designation: 242fa) and the like. 1,3,3-trichloro-1,1-difluoropropane (242fa), which is present as an intermediate product in a catalyst-free liquid-phase fluorination reaction for producing 1233zd from 240fa, is problematic especially because it reduces the productivity due to its accumulation in a reaction vessel as a result of its extremely low fluorinating reaction rate.

Japanese Patent Application Laid-Open No. H9-183740 employs a solid fluorinating catalyst, which should be watched to avoid inactivation and also should be packed again.

Japanese Patent Application Laid-Open No. H11-180908 employs 240fa to produce 1233zd and/or 1,3,3,3-tetrafluoropropene (abbreviated designation: 1234ze) by a catalyst-free gas-phase fluorinating reaction, which requires a prolonged heating at a high temperature.

SUMMARY

The present invention solves such problems and provides a method for producing trans-1-chloro-3,3,3-trifluoropropene efficiently from an intermediate product having a low reactivity.

The present invention comprises the following Inventions 1 to 17.

<Invention 1>

A method for producing trans-1-chloro-3,3,3-trifluoropropene comprising:

reacting a halogenated hydrocarbon compound having 3 carbon atoms represented by Formula (1):

$$C_3H_XCl_YF_Z \quad (1)$$

in a gas phase with hydrogen fluoride in the presence of chlorine, wherein X is 2 or 3; and when X=2, Y is an integer from 1 to 4, Z is an integer from 0 to 3, and Y+Z=4; and when X=3, Y is an integer from 1 to 5, Z is an integer from 0 to 4, and Y+Z=5; provided that Formula (1) shown above represents a halogenated hydrocarbon compound having 3 carbon atoms excluding trans-1-chloro-3,3,3-trifluoropropene.

<Invention 2>

The production method according to Invention 1 wherein a hydrocarbon compound having 3 carbon atoms represented by Formula (2):

$$C_3H_VF_W \quad (2)$$

is further added and reacted in a gas phase with hydrogen fluoride in the presence of chlorine, wherein when V+W=8, then V is an integer from 0 to 8; when V+W=6, then V is an integer from 0 to 6; and when V+W=4, then V is an integer from 0 to 4.

<Invention 3>

The production method according Inventions 1 or 2 wherein the aforementioned halogenated hydrocarbon compound having 3 carbon atoms is at least one selected from the group consisting of 1,1,3,3-tetrachloro-1-fluoropropane (241fa), 1,1,1,3-tetrachloro-3-fluoropropane (241fb), 1,3,3-trichloro-3-fluoropropene (1231zd), 1,3,3-trichloro-1-fluoropropene (1231zb), 3,3,3-trichloro-1-fluoropropene (1231ze), 1,1,3-trichloro-3-fluoropropene (1231za), 1,3,3-trichloro-1,1-difluoropropane (242fa), 1,1,3-trichloro-1,3-difluoropropane (242fb), 1,3-dichloro-3,3-difluoropropene (1232zd), 3,3-dichloro-1,3-difluoropropene (1232ze), 3,3-dichloro-1,1-difluoropropene (1232zc), 1,3-dichloro-1,3-difluoropropene (1232zb), cis-1-chloro-3,3,3-trifluoropropene (1233zd(Z)), 3,3-dichloro-1,1,1-trifluoropropane (243fa), 1,3-dichloro-1,1,3-trifluoropropane (243fb), 1,1-dichloro-1,3,3-trifluoropropane (243fc), 1-chloro-1,1,3,3-tetrafluoropropane (244fb) and 3-chloro-1,1,1,3-tetrafluoropropane (244fa).

<Invention 4>
The production method according to any one of Inventions 1 to 3 wherein the reaction temperature is 150° C. or higher and 600° C. or lower.
<Invention 5>
A method for producing trans-1-chloro-3,3,3-trifluoropropene comprising reacting at least one halogenated hydrocarbon compound selected from the group consisting of 1,1,3,3-tetrachloro-1-fluoropropane (241fa), 1,1,1,3,3-pentachloropropane, 1,3,3-trichloro-1,1-difluoropropane (242fa) in a gas phase with hydrogen fluoride at 150° C. or higher and 600° C. or lower in the presence of chlorine.
<Invention 6>
The production method according to Invention 5 wherein a hydrocarbon compound having 3 carbon atoms represented by Formula (3):

$$C_3H_VF_W \quad (3)$$

is further added and reacted in a gas phase with hydrogen fluoride in the presence of chlorine,
wherein when V+W=8, then V is an integer from 0 to 8; when V+W=6, then V is an integer from 0 to 6; and when V+W=4, then V is an integer from 0 to 4.
<Invention 7>
A method for producing trans-1-chloro-3,3,3-trifluoropropene comprising Step (A) for reacting 1,1,1,3,3-pentachloropropane (240fa) with hydrogen fluoride and Step (B) for reacting an intermediate product obtained in the aforementioned Step (A) in a gas phase with hydrogen fluoride at 150° C. or higher and 600° C. or lower in the presence of chlorine to obtain trans-1-chloro-3,3,3-trifluoropropene.
<Invention 8>
The production method according to Invention 7 wherein a hydrocarbon compound having 3 carbon atoms represented by Formula (4):

$$C_3H_VF_W \quad (4)$$

is further added and reacted in a gas phase with hydrogen fluoride in the presence of chlorine,
wherein when V+W=8, then V is an integer from 0 to 8; when V+W=6, then V is an integer from 0 to 6; and when V+W=4, then V is an integer from 0 to 4.
<Invention 9>
The production method according to Invention 7 or 8 wherein
the aforementioned Step (A) is conducted under a catalyst-free condition in a liquid phase to recover a reaction product gas containing trans-1-chloro-3,3,3-trifluoropropene, and
the reaction fluid of the aforementioned Step (A) is recovered and the aforementioned intermediate product contained in said reaction fluid is employed in the aforementioned Step (B).
<Invention 10>
The production method according to Invention 9 wherein
the aforementioned 1,1,1,3,3-pentachloropropane and the aforementioned hydrogen fluoride are introduced continuously or intermittently to the aforementioned Step (A), and
the aforementioned reaction product gas and the aforementioned reaction fluid are recovered continuously or intermittently.
<Invention 11>
The production method according to any one of Inventions 7 to 10 wherein the aforementioned intermediate product is at least one selected from the group consisting of 1,1,3,3-tetrachloro-1-fluoropropane (241fa), 1,1,1,3-tetrachloro-3-fluoropropane (241fb), 1,3,3-trichloro-3-fluoropropene (1231zd), 1,3,3-trichloro-1-fluoropropene (1231zb), 3,3,3-trichloro-1-fluoropropene (1231ze), 1,1,3-trichloro-3-fluoropropene (1231za), 1,3,3-trichloro-1,1-difluoropropane (242fa), 1,1,3-trichloro-1,3-difluoropropane (242fb), 1,3-dichloro-3,3-difluoropropene (1232zd), 3,3-dichloro-1,3-difluoropropene (1232ze), 3,3-dichloro-1,1-difluoropropene (1232zc), 1,3-dichloro-1,3-difluoropropene (1232zb), cis-1-chloro-3,3,3-trifluoropropene (1233zd(Z)), 3,3-dichloro-1,1,1-trifluoropropane (243fa) and 3-chloro-1,1,1,3-tetrafluoropropane (244fa).
<Invention 12>
The production method according to any one of Inventions 7 to 11 wherein the aforementioned intermediate product at least comprises 1,3,3-trichloro-1,1-difluoropropane (242fa).
<Invention 13>
The production method according to any one of Inventions 7 to 12 wherein the reaction temperature of the aforementioned Step (B) is 150° C. or higher and 500° C. or lower.
<Invention 14>
The production method according to any one of Inventions 7 to 13 wherein an unreacted intermediate product is recovered and employed in the aforementioned Step (B).
<Invention 15>
The production method according to any one of Inventions 7 to 14 wherein cis-1-chloro-3,3,3-trifluoropropene is obtained in the aforementioned Step (B) together with trans-1-chloro-3,3,3-trifluoropropene.
<Invention 16>
The production method according to Invention 15 wherein cis-1-chloro-3,3,3-trifluoropropene obtained is subjected as an intermediate product to the aforementioned Step (B).
<Invention 17>
The production method according to Invention 15 wherein cis-1-chloro-3,3,3-trifluoropropene obtained is heated at 150° C. or higher and 600° C. or lower to obtain trans-1-chloro-3,3,3-trifluoropropene.

BRIEF DESCRIPTION OF DRAWINGS

FIG. 1 is a schematic view of a production device 100 according to one embodiment of the present invention.

REFERENCE SIGNS LIST

1 . . . valve, 2 . . . valve, 3 . . . valve, 4 . . . valve, 5 . . . valve, 6 . . . valve, 7 . . . valve, 8 . . . valve, 10 . . . liquid phase reaction chamber, 11 . . . pipe, 13 . . . pipe, 15 . . . pipe, 17 . . . pipe, 30 . . . condenser, 31 . . . pipe, 35 . . . condenser, 36 . . . pipe, 50 . . . tank, 70 . . . tank, 71 . . . pipe, 90 . . . gas phase reaction tower, 91 . . . pipe, 93 . . . pipe, 95 . . . pipe, 100 . . . production device

DESCRIPTION OF EMBODIMENTS

As a result of our intensive study, the inventors discovered that when an intermediate product such as 1,3,3-trichloro-1,1-difluoropropane which has an extremely low reactivity in a catalyst-free fluorinating reaction of 1,1,1,3,3-pentachloropropane in a liquid phase is heated in a gas phase together with hydrogen fluoride in the presence of a catalytic amount of chlorine outside of the reaction system, it can be converted into trans-1-chloro-3,3,3-trifluoropropene efficiently, thereby establishing the method for producing trans-1-chloro-3,3,3-trifluoropropene according to the invention.

Thus, in the method of the invention, an intermediate product accumulating in a reaction vessel is taken out and converted efficiently by a gas-phase fluorinating reaction in the presence of a catalytic amount of chlorine, thereby improving the productivity.

While the present invention is a method for producing trans-1-chloro-3,3,3-trifluoropropene (1233zd(E)) efficiently from an intermediate product such as 1,3,3-trichloro-1,1-difluoropropane (242fa) which has an extremely low reactivity in a catalyst-free fluorinating reaction of 1,1,1,3,3-pentachloropropane (240fa) in a liquid phase, which is, however, not limitative. Thus, the present invention is a method for producing trans-1-chloro-3,3,3-trifluoropropene using a halogenated hydrocarbon compound having 3 carbon atoms as a starting material by reacting with hydrogen fluoride in the presence of a catalytic amount of chlorine.

The halogenated hydrocarbon compound having 3 carbon atoms employed in the present invention is a halogenated hydrocarbon compound having 3 carbon atoms represented by Formula (5):

$$C_3H_XCl_YF_Z \quad (5)$$

wherein X is 2 or 3; and when X=2, Y is an integer from 1 to 4, Z is an integer from 0 to 3, and Y+Z=4; and when X=3, Y is an integer from 1 to 5, Z is an integer from 0 to 4, and Y+Z=5; provided that Formula (5) represents a halogenated hydrocarbon compound having 3 carbon atoms excluding trans-1-chloro-3,3,3-trifluoropropene.

The halogenated hydrocarbon compound having 3 carbon atoms represented by Formula (5), when X=2, is $C_3H_2Cl_1F_3$, $C_3H_2Cl_2F_2$, $C_3H_2Cl_3F_1$, $C_3H_2Cl_4$, and, when X=3, is $C_3H_3Cl_1F_4$, $C_3H_3Cl_2F_3$, $C_3H_3Cl_3F_2$, $C_3H_3Cl_4F_1$, $C_3H_3Cl_5$.

The halogenated hydrocarbon compound having 3 carbon atoms which is a starting material employed in the invention is typically one selected from the group consisting of 1,1,3,3-tetrachloro-1-fluoropropane (abbreviated designation: 241fa), 1,1,1,3-tetrachloro-3-fluoropropane (abbreviated designation: 241fb), 1,3,3-trichloro-3-fluoropropene (abbreviated designation: 1231zd), 1,3,3-trichloro-1-fluoropropene (abbreviated designation: 1231zb), 3,3,3-trichloro-1-fluoropropene (abbreviated designation: 1231ze), 1,1,3-trichloro-3-fluoropropene (abbreviated designation: 1231za), 1,3,3-trichloro-1,1-difluoropropane (242fa), 1,1,3-trichloro-1,3-difluoropropane (abbreviated designation: 242fb), 1,3-dichloro-3,3-difluoropropene (abbreviated designation: 1232zd), 3,3-dichloro-1,3-difluoropropene (abbreviated designation: 1232ze), 3,3-dichloro-1,1-difluoropropene (abbreviated designation: 1232zc), 1,3-dichloro-1,3-difluoropropene (abbreviated designation: 1232zb), cis-1-chloro-3,3,3-trifluoropropene (1233zd(Z)), 3,3-dichloro-1,1,1-trifluoropropane (abbreviated designation: 243fa), 1,3-dichloro-1,1,3-trifluoropropane (abbreviated designation: 243fb), 1,1-dichloro-1,3,3-trifluoropropane (abbreviated designation: 243fc), 1-chloro-1,1,3,3-tetrafluoropropane (abbreviated designation: 244fb) and 3-chloro-1,1,1,3-tetrafluoropropane (abbreviated designation: 244fa).

Although a reaction fluid after conducting a catalyst-free fluorinating reaction of 1,1,1,3,3-pentachloropropane in a liquid phase contains a trace amount of trans-1-chloro-3,3,3-trifluoropropene, the reaction starting from trans-1-chloro-3,3,3-trifluoropropene to synthesize trans-1-chloro-3,3,3-trifluoropropene itself does not serve as a production method, and accordingly is excluded here in this specification.

It is possible to use a hydrocarbon compound having 3 carbon atoms together with a halogenated hydrocarbon compound having 3 carbon atoms which is a reaction starting material employed in the invention. As a result of the effect of a chlorine source such as hydrogen chloride and chlorine radical derived from a halogenated hydrocarbon compound, the hydrocarbon compound having 3 carbon atoms can also be converted into trans-1-chloro-3,3,3-trifluoropropene. The hydrocarbon compound having 3 carbon atoms is represented by Formula (6):

$$C_3H_VF_W \quad (6)$$

wherein when V+W=8, then V is an integer from 0 to 8; when V+W=6, then V is an integer from 0 to 6; and when V+W=4, then V is an integer from 0 to 4.

The hydrocarbon compound having 3 carbon atoms represented by Formula (6), when V+W=8, is $C_3F_8$, $C_3H_1F_7$, $C_3H_2F_6$, $C_3H_3F_5$, $C_3H_4F_4$, $C_3H_5F_3$, $C_3H_6F_2$, $C_3H_7F_1$, $C_3H_8$, and, when V+W=6, is $C_3F_6$, $C_3H_1F_5$, $C_3H_2F_4$, $C_3H_3F_3$, $C_3H_4F_2$, $C_3H_5F_1$, $C_3H_6$, and when V+W=4, is $C_3F_4$, $C_3H_1F_3$, $C_3H_2F_2$, $C_3H_3F_1$, $C_3H_4$.

Typically, the hydrocarbon compound having 3 carbon atoms may for example be 1,1,1,3,3-pentafluoropropane (abbreviated designation: 245fa), trans-1,3,3,3-tetrafluoropropene (abbreviated designation: 1234ze(E)), cis-1,3,3,3-tetrafluoropropene (abbreviated designation: 1234ze(Z)), 1,1,3,3-tetrafluoropropene (abbreviated designation: 1234zc), 3,3,3-trifluoropropine and the like.

The halogenated hydrocarbon compound having 3 carbon atoms as a starting material is not limited to a reaction product of a catalyst-free fluorinating reaction of 1,1,1,3,3-pentachloropropane (240fa) in a liquid phase, and may be produced by any method. For example, a method in which 1,1,1,3,3-pentachloropropane and hydrogen fluoride are introduced into a fluorinated chromium oxide catalyst at 250° C. thereby effecting fluorination (see Japanese Patent Application Laid-Open No. H9-183740), and a method in which 1,1,1,3,3-pentachloropropane and hydrogen fluoride are reacted for 5 hours at 200° C. under 100 kg/cm² (about 10 MPa) in a liquid phase (See Japanese Patent Application Laid-Open No. H11-180908) may be exemplified.

While the molar ratio of halogenated hydrocarbon compound having 3 carbon atoms/hydrogen fluoride to be supplied to the reaction region varies depending on reaction temperature, it is 1/1 to 1/20, preferably 1/1 to 1/10. Such a molar ratio is not limited to be within a strict numerical value range, and should be understood to be about 1/1 to about 1/20, preferably about 1/1 to about 1/10. An amount of hydrogen fluoride which exceeds 20-molar amount of a halogenated hydrocarbon compound having 3 carbon atoms results in a reduction in organic substance treatment quantity in an identical single reaction vessel and causes a difficulty in separation of a mixture of unreacted hydrogen fluoride and a product which exited from the reaction system. On the other hand, an amount of hydrogen fluoride which is less than 1-molar amount results in a reduction in the reaction rate, which leads to a problematic reduction in the selection rate.

While the molar ratio of halogenated hydrocarbon compound having 3 carbon atoms/chlorine to be supplied to the reaction region varies depending on reaction temperature, it is 1/0.001 to 1/0.5, preferably 1/0.01 to 1/0.1, most preferably 1/0.01 to 1/0.03. Such a molar ratio is not limited to be within a strict numerical value range, and should be understood to be about 1/0.001 to about 1/0.5, preferably about 1/0.01 to about 1/0.1. An amount of chlorine which exceeds 0.5-molar amount of a halogenated hydrocarbon compound having 3 carbon atoms results in a problematic increase in the production of perchlorinated substances. On the other hand, an amount of chlorine which is less than 0.001-molar amount results in a reduction in the reaction rate, which leads to a problematic reduction in the conversion rate.

It is preferable to use hydrogen fluoride in an excessive amount because the conversion rate of a halogenated hydrocarbon compound having 3 carbon atoms is increased. Any unreacted hydrogen fluoride is separated from unreacted organic substances and reaction products and then recycled to the reaction system. The separation of hydrogen fluoride from the organic substances can be conducted by any known means.

The temperature at which the reaction according to the invention is not limited particularly, it is 150° C. or higher and 600° C. or lower, preferably 150° C. or higher and 500° C. or lower, more preferably 250° C. or higher and 400° C. or lower. The reaction temperature is not limited to be within a strict numerical value range, and should be understood to be about 150 to about 600° C., preferably about 150 to about 500° C., more preferably about 250 to about 400° C. A reaction temperature below 150° C. is not practical because it allows the reaction to proceed slowly. On the other hand, a temperature exceeding 600° C. is not preferable since it causes tar formation and increases degradation products.

In the reaction according to the invention, the halogenated hydrocarbon compound having 3 carbon atoms to be supplied to the reaction region may be supplied together with a gas having no effect on the reaction, such as nitrogen, helium, argon and the like. Such a gas is used in an amount, per 1 mole of halogenated hydrocarbon compound having 3 carbon atoms, of 100 moles or less, preferably 10 moles or less. Such an amount is not limited to be within a strict numerical value range, and should be understood to be about 100 moles or less, preferably about 10 moles or less. Since the reaction according to the invention is conducted in a gas phase, it is preferable usually to avoid use of the gas having no effect on the reaction which dilutes the starting materials.

The pressure at which the reaction according to the invention is conducted is not limited particularly. An atmospheric pressure can be employed, i.e., there is no need of any pressure adjustment such as pressurization or depressurization. From the viewpoint of devices, 0.01 to 1 MPa (indicated here and hereinafter as absolute pressures) is employed preferably. Since pressurization allows the equilibration to be biased toward addition reaction, depressurization may be employed. When establishing the pressure, it is desirable to select a condition under which any organic substance existing in the system, such as a starting material, is not liquefied in the reaction system.

The exposure time of the reaction (reaction time) according to the invention in a standard state (0° C., 1 atm) is usually 0.1 to 500 seconds, preferably 10 to 300 seconds. A shorter exposure time leads to a reduced reaction rate, while a longer exposure time leads to a problematic side effect.

The reaction according to the invention is conducted by introducing halogenated hydrocarbon compound having 3 carbon atoms, hydrogen fluoride and chlorine into a reaction vessel substantially at the same time while controlling the temperature. The reaction vessel is usually in a tubular shape and made from stainless steel, Hastelloy™, Monel™, platinum, carbon, fluorine resin or materials lined therewith. While the reaction vessel may be a hollow tube, it may be packed with the aforementioned materials for the purpose of improving the heat exchange efficiency.

Also in the present invention, the halogenated hydrocarbon compound having 3 carbon atoms is preferably at least one selected from the group consisting of 1,1,3,3-tetrachloro-1-fluoropropane (241fa), 1,1,1,3,3-pentachloropropane (240fa), 1,3,3-trichloro-1,1-difluoropropane (242fa). When such a halogenated hydrocarbon compound having 3 carbon atoms is used as a starting organic substance, it is possible to produce trans-1-chloro-3,3,3-trifluoropropene by a reaction in a gas phase with hydrogen fluoride at a predetermined reaction temperature in the presence of chlorine. The reaction temperature employed here is 150° C. or higher and 600° C. or lower, preferably 150° C. or higher and 500° C. or lower, more preferably 250° C. or higher and 400° C. or lower. The reaction temperature is not limited to be within a strict numerical value range, and should be understood to be about 150 to about 600° C., preferably about 150 to about 500° C., more preferably about 250 to about 400° C. A reaction temperature below 150° C. is not practical because it allows the reaction to proceed slowly. On the other hand, a temperature exceeding 600° C. is not preferable since it causes tar formation and increases degradation products.

(Production Method Using 1,1,1,3,3-Pentachloropropane)

A method using 1,1,1,3,3-pentachloropropane (240fa) as a starting organic substance to produce trans-1-chloro-3,3,3-trifluoropropene is described below. The production method according to one embodiment of the present invention comprises Step (A) for reacting 1,1,1,3,3-pentachloropropane (240fa) with hydrogen fluoride and Step (B) for reacting an intermediate product obtained in the aforementioned Step (A) in a gas phase with hydrogen fluoride in the presence of chlorine to obtain trans-1-chloro-3,3,3-trifluoropropene.

FIG. 1 is a schematic view of a production device 100 according to one embodiment. The production device 100 is provided, for example, with a liquid phase reaction chamber 10, a condenser 30, a tank 50, a tank 70 and a gas phase reaction tower 90, which are however not limitative. The liquid phase reaction chamber 10 may for example be a stainless steel autoclave, to which the starting organic substance is supplied from a pipe 11 via a valve 1. Also to the liquid phase reaction chamber 10, hydrogen fluoride is supplied from a pipe 13 via a valve 2. While the starting organic substance and hydrogen fluoride are exemplified in FIG. 1 to be supplied from discrete pipes, they may be supplied from a single pipe individually or as a mixture to the liquid phase reaction chamber 10.

The top of the liquid phase reaction chamber 10 is connected to a pipe 15, which is connected to a condenser 30. The condenser 30 is connected to a pipe 31, which is connected via a valve 3 to a tank 50. The tank 50 stores trans-1-chloro-3,3,3-trifluoropropene which is liquefied in the condenser 30. The liquid phase reaction chamber 10 is connected at its bottom to a pipe 17 which is connected via a valve 4 to a tank 70. The tank 70 stores a reaction fluid containing the intermediate product produced in the liquid phase reaction chamber 10.

A pipe 71 connected to the tank 70 is connected via a valve 5 to a gas phase reaction tower 90. To the gas phase reaction tower 90, a pipe 91 is connected via a valve 6 and supplies chlorine to the gas phase reaction tower 90. Also to the gas phase reaction tower 90, a pipe 93 is connected via a valve 7 and supplies hydrogen fluoride to the gas phase reaction tower 90. While chlorine and hydrogen fluoride are indicated in FIG. 1 as being supplied from discrete pipes, they may be supplied from a single pipe individually or as a mixture to the gas phase reaction tower 90.

The gas phase reaction tower 90 is connected at its tip with a pipe 95 which is connected via a valve 8 to a condenser 35. The condenser 35 is connected via a pipe 36 to the tank 50. The tank 50 stores trans-1-chloro-3,3,3- trifluoropropene which is liquefied in a condenser 35. While the trans-1-chloro-3,3,3-trifluoropropene produced in 2 systems are indicated in FIG. 1 as being stored in a common tank 50, they may be stored in discrete tanks.

The production method according to one embodiment of the present invention may comprise Step (A) for reacting 1,1,1,3,3-pentachloropropane (240fa) with hydrogen fluoride in the liquid phase reaction chamber 10 and Step (B) for allowing an intermediate product obtained in the aforementioned Step (A) to be introduced into gas phase reaction tower 90 and reacted in a gas phase with hydrogen fluoride in the presence of chlorine to obtain trans-1-chloro-3,3,3-trifluoropropene. The reaction product gas containing trans-1-chloro-3,3,3-trifluoropropene produced in the liquid phase reaction chamber 10 is taken via the pipe 15 out of the liquid phase reaction chamber 10 and liquefied in the condenser 30 and then recovered into the tank 50. The introduction of 1,1,1,3,3-pentachloropropane (240fa) and hydrogen fluoride may be conducted continuously, or may be conducted intermittently while opening and closing the valve 3. The recovery of trans-1-chloro-3,3,3-trifluoropropene may be conducted continuously, or may be conducted intermittently while opening and closing the valve 3.

On the other hand, the reaction fluid containing the intermediate product produced in the liquid phase reaction chamber 10 is recovered via the pipe 17 into the tank 70. The reaction fluid stored in the tank 70 is supplied via the pipe 71 to the gas phase reaction tower 90. In the gas phase reaction tower 90 an intermediate product (aforementioned halogenated hydrocarbon compound having 3 carbon atoms) contained in the reaction fluid and hydrogen fluoride are reacted in a gas phase in the presence of chlorine to produce trans-1-chloro-3,3,3-trifluoropropene. Here, the reaction fluid stored in the tank 70 may further be combined with the aforementioned hydrocarbon compound having 3 carbon atoms, which is reacted as a reaction starting material with hydrogen fluoride in the gas phase reaction tower 90. The reaction product gas containing trans-1-chloro-3,3,3-trifluoropropene produced in the gas phase reaction tower 90 is taken via the pipe 95 out of the gas phase reaction tower 90 and liquefied in the condenser 35 and recovered via the pipe 36 into the tank 50.

The method for reacting 1,1,1,3,3-pentachloropropane with hydrogen fluoride is not limited to the aforementioned embodiment, and any known methods may be employed. Examples include, but are not limited to, a gas-phase reaction method (see Japanese Patent Application Laid-Open No. H9-183740), and a liquid-phase reaction method (See Japanese Patent Application Laid-Open No. H11-180908). The intermediate product obtained by reacting 1,1,1,3,3-pentachloropropane with hydrogen fluoride is reacted with hydrogen fluoride in a gas phase in the presence of chlorine, thereby producing trans-1-chloro-3,3,3-trifluoropropane. Here, the method for reacting the intermediate product with hydrogen fluoride in a gas phase in the presence of chlorine can be described in accordance with the method for reacting the halogenated hydrocarbon compound having 3 carbon atoms with hydrogen fluoride in a gas phase in the presence of chlorine as described above. Thus, it can be described by replacing "halogenated hydrocarbon compound having 3 carbon atoms" with "intermediate product".

In the reaction mixture obtained by the reaction in Step (B), the aforementioned intermediate product which was not reacted or any reaction by-products may be contained in addition to the intended trans-1-chloro-3,3,3-trifluoropropene. They may be taken out and supplied to the reaction system of Step (B) where they may further be reacted. As a result, the intended trans-1-chloro-3,3,3-trifluoropropene can efficiently be produced.

The method for separating trans-1-chloro-3,3,3-trifluoropropene from this reaction mixture is not limited particularly. The separation may be conducted for example by distillation. It is also possible, if necessary in order to accomplish the separation easily, to remove acidic components possibly contained in the reaction mixture by means of washing with water.

While Step (B) gives the intended trans-1-chloro-3,3,3-trifluoropropene, it is possible that cis-1-chloro-3,3,3-trifluoropropene is produced concomitantly. In such a case, cis-1-chloro-3,3,3-trifluoropropene may be taken out of the reaction mixture and supplied to the reaction system of Step (B) and further reacted as described above, or may also heated separately at 150° C. or higher and 600° C. or lower to effect isomerization thereby producing trans-1-chloro-3,3,3-trifluoropropene.

In the method according to the invention, a solid catalyst may be employed or may not be employed. When no solid catalyst is employed, any problems such as inactivation of the catalyst or re-packing of the catalyst can be avoided, and trans-1-chloro-3,3,3-trifluoropropene can be produced at a low cost by a simple procedure.

Such a gas-phase reaction of halogenated hydrocarbon compound having 3 carbon atoms and hydrogen fluoride in the presence of chlorine according to the invention is not known, and is a novel synthetic route. In one embodiment of the invention, synthesis of trans-1-chloro-3,3,3-trifluoropropene in at least two systems enables a highly efficient consumption even of an intermediate product having a low reactivity, thereby enabling an efficient synthesis of trans-1-chloro-3,3,3-trifluoropropene from 1,1,1,3,3-pentachloropropane (240fa) as a starting material.

EXAMPLES

The method of producing trans-1-chloro-3,3,3-trifluoropropene of the invention is described in the following Examples, to which the invention is not limited.

Preparation Example 1

To a 2000-ml stainless steel autoclave fitted with a condenser through which a cooling fluid at 100° C. was circulated, 1,1,1,3,3-pentachloropropane (240fa) at 4.1 g/min and hydrogen fluoride at 3.4 g/min (molar ratio: 240 fa/hydrogen fluoride=about 1/9) were introduced and the autoclave was heated at 150° C. At the time when the pressure exceeded about 4 MPa, the reaction product gas was exhausted from the needle valve at the exit of the condenser so that about 4 MPa was maintained. The exhausted gas was passed through a gas washing bottle made from a fluorine resin which was cooled in an ice bath and which contained ice water thereby absorbing acids, and the reaction product organic substances were recovered in a glass trap in a dry ice-acetone bath. When the quantity of the fluid in the autoclave reached about 1000 ml, the reaction fluid was drained via a needle valve from the dip tube so that about 1000 ml was maintained. The drained reaction fluid was recovered into a gas washing bottle made from a fluorine resin which was cooled in an ice bath and which contained ice water. After continuing the reaction for 24 hours, the reaction fluid in the autoclave was recovered entirely into the gas washing bottle made from a fluorine resin containing ice water. The amount of the reaction product organic substance recovered from the outlet of the condenser was 2923 g in total, and the amount of the reaction fluid drained from the dip tube was 1871 g in total. The results of gas chromatography analysis are shown in Table 1. In Table 1, 1233E stands for trans-1-chloro-3,3,3-trifluoropropene (1233zd(E)), and 1233Z stands for cis-1-chloro-3,3,3-trifluoropropene (1233zd(Z)).

TABLE 1

|  | GC area % | | | | | | |
|---|---|---|---|---|---|---|---|
|  | 1233E | 244fa | 1233Z | 243fa | 242fa | 241fa | 240fa |
| Reaction product gas | 84.29 | 0.93 | 5.33 | 0.16 | 4.37 | 2.88 | 0.17 |
| Reaction fluid | 0.36 | 1.41 | 2.04 | 1.55 | 24.49 | 56.58 | 1.2 |

Example 1

To a 40 cm-long cylindrical stainless steel (SUS316L) reaction tube fitted with an electric furnace and having an inner diameter of 2.7 cm, nitrogen was passed at 10 ml/min while raising the temperature. At the time when the temperature of the reaction tube reached 320° C., the reaction starting materials consisting of the reaction fluid (halogenated hydrocarbon compound having 3 carbon atoms) of Preparation Example 1 in a gas state at about 0.32 g/min, hydrogen fluoride at about 0.12 g/min, chlorine at about 0.8 ml/min were supplied respectively (molar ratio: halogenated hydrocarbon compound having 3 carbon atoms/hydrogen fluoride/chlorine=1/3.4/0.02, exposure time: about 50 seconds), and when the flow rates were stabilized, nitrogen supply was terminated. The product gas coming from the reaction vessel was passed through a gas washing bottle made from a fluorine resin which was cooled in an ice bath and which contained ice water thereby absorbing unreacted hydrogen fluoride and hydrogen chloride and trapping the reaction product. The results of the analysis of the trapped reaction product by gas chromatography are shown in Table 3. In Table 3, 1234E stands for trans-1,3,3,3-tetrafluoropropene (1234ze(E)), 1234Z stands for cis-1,3,3,3-tetrafluoropropene (1234ze(Z)), 1233E stands for trans-1-chloro-3,3,3-trifluoropropene (1233zd(E)), 1233Z stands for cis-1-chloro-3,3,3-trifluoropropene (1233zd(Z)).

Example 2

Except that the amounts of the reaction starting material to be supplied were changed here to supply the reaction fluid (halogenated hydrocarbon compound having 3 carbon atoms) of Preparation Example 1 in a gas state at about 0.47 g/min, hydrogen fluoride at about 0.10 g/min, chlorine at about 0.8 ml/min (molar ratio :halogenated hydrocarbon compound having 3 carbon atoms/hydrogen fluoride/chlorine=1/2.0/0.02, exposure time: about 50 seconds), the reaction was conducted similarly to Example 1. The results are shown in Table 3.

Example 3

Except for supplying the reaction starting materials at the time when the temperature of the reaction tube reached 150° C., the reaction was conducted similarly to Example 1. The results are shown in Table 3.

Example 4

Except for supplying the reaction starting materials at the time when the temperature of the reaction tube reached 250° C., the reaction was conducted similarly to Example 1. The results are shown in Table 3.

Example 5

Except that the amounts of the reaction starting material to be supplied were changed here to supply the reaction fluid (halogenated hydrocarbon compound having 3 carbon atoms) of Preparation Example 1 in a gas state at about 0.32 g/min, hydrogen fluoride at about 0.12 g/min, chlorine at about 0.4 ml/min (molar ratio: halogenated hydrocarbon compound having 3 carbon atoms/hydrogen fluoride/chlorine=1/3.4/0.01, exposure time: about 50 seconds), the reaction was conducted similarly to Example 1. The results are shown in Table 3.

Example 6

Except that the amounts of the reaction starting material to be supplied were changed here to supply the reaction fluid (halogenated hydrocarbon compound having 3 carbon atoms) of Preparation Example 1 in a gas state at about 0.32 g/min, hydrogen fluoride at about 0.12 g/min, chlorine at about 1.2 ml/min (molar ratio: halogenated hydrocarbon compound having 3 carbon atoms/hydrogen fluoride/chlorine=1/3.4/0.03, exposure time: about 50 seconds), the reaction was conducted similarly to Example 1. The results are shown in Table 3.

The reaction temperatures, exposure times and the amounts of the reaction starting materials supplied in Examples 1 to 6 and following Comparative Examples 1 to 2 are summarized in Table 2.

TABLE 2

| | Reaction | | Average flow rate (molar ratio) | | |
|---|---|---|---|---|---|
| | temperature (° C.) | Exposure time (s) | Reaction fluid | Hydrogen fluoride | Chlorine |
| Example 1 | 320 | 50 | 1 | 3.4 | 0.020 |
| Example 2 | 320 | 50 | 1 | 2 | 0.020 |
| Example 3 | 150 | 50 | 1 | 3.4 | 0.020 |
| Example 4 | 250 | 50 | 1 | 3.4 | 0.020 |
| Example 5 | 320 | 50 | 1 | 3.4 | 0.010 |
| Example 6 | 320 | 50 | 1 | 3.4 | 0.030 |
| Comparative Example 1 | 320 | 50 | 1 | 3.4 | 0.000 |
| Comparative Example 2 | 100 | 50 | 1 | 3.4 | 0.020 |

TABLE 3

| | GC area % | | | | | | | | | | |
|---|---|---|---|---|---|---|---|---|---|---|---|
| | 1234E | 245fa | 1234Z | 1233xf | 1233E | 244fa | 1233Z | 243fa | 242fa | 241fa | total |
| Reaction fluid | 0.01 | 0.00 | 0.00 | 0.00 | 0.36 | 1.14 | 2.04 | 1.55 | 24.49 | 56.58 | 86.43 |
| Example 1 | 1.17 | 1.78 | 0.29 | 1.21 | 68.52 | 2.4 | 9.59 | 3.65 | 3.42 | 0.04 | 92.07 |
| Example 2 | 0.5 | 0.39 | 0.11 | 0.56 | 66.68 | 1.68 | 9.15 | 3.97 | 7.93 | 0.05 | 91.02 |
| Example 3 | 0.28 | 0.26 | 0.12 | 0.33 | 28.65 | 2.86 | 6.51 | 6.12 | 19.55 | 18.69 | 83.37 |
| Example 4 | 0.52 | 0.26 | 0.16 | 0.26 | 55.17 | 2.13 | 10.1 | 4.99 | 16.56 | 0.45 | 90.6 |
| Example 5 | 1.06 | 1.59 | 0.22 | 1.16 | 64.92 | 2.91 | 9.03 | 3.85 | 5.66 | 2.58 | 92.98 |
| Example 6 | 1.11 | 1.8 | 0.28 | 1.36 | 69.04 | 1.92 | 9.63 | 2.67 | 2.51 | 0.02 | 90.34 |
| Comparative Example 1 | 0.11 | 0.1 | 0.01 | 0.02 | 9.52 | 2.24 | 3.05 | 3.67 | 23.45 | 43.97 | 86.14 |
| Comparative Example 2 | 0.03 | 0.06 | 0.00 | 0.05 | 6.12 | 1.76 | 2.87 | 1.72 | 23.89 | 48.69 | 85.19 |

Comparative Example 1

Except that the amounts of the reaction starting material to be supplied were changed here to supply the reaction fluid (halogenated hydrocarbon compound having 3 carbon atoms) of Preparation Example 1 in a gas state at about 0.32 g/min, hydrogen fluoride at about 0.12 g/min (molar ratio: halogenated hydrocarbon compound having 3 carbon atoms/hydrogen fluoride=1/3.4, exposure time: about 50 seconds), the reaction was conducted similarly to Example 1. The results are shown in Table 3.

Comparative Example 2

Except for supplying the reaction starting materials at the time when the temperature of the reaction tube reached 100° C., the reaction was conducted similarly to Example 1. The results are shown in Table 3.

As evident from Comparative Example 1, when chlorine was not supplied as a reaction starting material, there was almost no conversion from 242fa or 241fa into 1233zd(E) even with heating at a high temperature. As evident from Comparative Example 2, even when chlorine was supplied as a reaction starting material, no sufficient progression of the reaction was achieved at a heating temperature around 100° C., allowing 242fa or 241fa to be remaining.

In the production method of producing trans-1-chloro-3,3,3-trifluoropropene according to the present invention, an intermediate product such as 1,3,3-trichloro-1,1-difluoropropane which has an extremely low reactivity in a catalyst-free fluorinating reaction of 1,1,1,3,3-pentachloropropane in a liquid phase is heated in a gas phase together with hydrogen fluoride in the presence of a catalytic amount of chlorine outside of the reaction system, thereby producing trans-1-chloro-3,3,3-trifluoropropene efficiently.

What is claimed is:

1. A method for producing trans-1-chloro-3,3,3-trifluoropropene comprising:
reacting a starting material containing a plurality of halogenated hydrocarbon compounds, each having 3 carbon atoms of Formula (1):

$$C_3H_XCl_YF_Z \quad (1)$$

in a gas phase with hydrogen fluoride in the presence of chlorine as a catalyst,
wherein X is 2 or 3; and when X=2, Y is an integer from 1 to 4, Z is an integer from 0 to 3, and Y+Z=4; and when X=3, Y is an integer from 1 to 5, Z is an integer from 0 to 4, and Y+Z=5; provided that Formula (1) shown above represents a halogenated hydrocarbon compound having 3 carbon atoms excluding trans-1-chloro-3,3,3-trifluoropropene.

2. The production method according to claim 1 wherein a hydrocarbon compound having 3 carbon atoms of Formula (2):

$$C_3H_VF_W \quad (2)$$

is further added and reacted in a gas phase with hydrogen fluoride in the presence of chlorine,
wherein when V+W=8, then V is an integer from 0 to 8; when V+W=6, then V is an integer from 0 to 6; and when V+W=4, then V is an integer from 0 to 4.

3. The production method according to claim 1 wherein each of the plurality of halogenated hydrocarbon compounds having 3 carbon atoms is selected from the group consisting of 1,1,3,3-tetrachloro-1-fluoropropane (241fa), 1,1,1,3-tetrachloro-3-fluoropropane (241fb), 1,3,3-trichloro-3-fluoropropene (1231zd), 1,3,3-trichloro-1-fluoropropene (1231zb), 3,3,3-trichloro-1-fluoropropene (1231ze), 1,1,3-trichloro-3-fluoropropene (1231za), 1,3,3-trichloro-1,1-difluoropropane (242fa), 1,1,3-trichloro-1,3-difluoropropane (242fb), 1,3-dichloro-3,3-difluoropropene (1232zd), 3,3-dichloro-1,3-difluoropropene (1232ze), 3,3-dichloro-1,1-difluoropropene (1232zc), 1,3-dichloro-1,3-difluoropropene (1232zb), cis-1-chloro-3,3,3-trifluoropropene (1233zd(Z)), 3,3-dichloro-1,1,1-trifluoropropane (243fa) and 3-chloro-1,1,1,3-tetrafluoropropane (244fa).

4. The production method according to claim 1 wherein the reaction temperature is from 150° C. to 600° C.

5. A method for producing trans-1-chloro-3,3,3-trifluoropropene comprising reacting a starting material containing a plurality of halogenated hydrocarbon compounds, each selected from the group consisting of 1,1,3,3-tetrachloro-1-fluoropropane (241fa), 1,1,1,3,3-pentachloropropane (240fa), 1,3,3-trichloro-1,1-difluoropropane (242fa) in a gas phase with hydrogen fluoride as a catalyst at a temperature from 150° C. to 600° C. in the presence of chlorine as a catalyst.

6. The production method according to claim 5 wherein a hydrocarbon compound having 3 carbon atoms of Formula (3):

$$C_3H_VF_W \quad (3)$$

is further added and reacted in a gas phase with hydrogen fluoride in the presence of chlorine,
wherein when V+W=8, then V is an integer from 0 to 8; when V+W=6, then V is an integer from 0 to 6; and when V+W=4, then V is an integer from 0 to 4.

7. A method for producing trans-1-chloro-3,3,3-trifluoropropene comprising:

Step (A) for reacting 1,1,1,3,3-pentachloropropane (240fa) with hydrogen fluoride, and Step (B) for reacting a plurality of intermediate products, each obtained in the Step (A) in a gas phase with hydrogen fluoride at a temperature from 150° C. to 600° C. in the presence of chlorine as a catalyst to obtain trans-1-chloro-3,3,3-trifluoropropene.

8. The production method according to claim 7 wherein a hydrocarbon compound having 3 carbon atoms of Formula (4):

$$C_3H_VF_W \quad (4)$$

is further added and reacted in a gas phase with hydrogen fluoride in the presence of chlorine, wherein when V+W=8, then V is an integer from 0 to 8; when V+W=6, then V is an integer from 0 to 6; and when V+W=4, then V is an integer from 0 to 4.

9. The production method according to claim 7 wherein the Step (A) is conducted under a catalyst-free condition in a liquid phase to recover a reaction product gas containing trans-1-chloro-3,3,3-trifluoropropene, and the reaction fluid of the Step (A) is recovered and the intermediate products contained in said reaction fluid are employed in the Step (B).

10. The production method according to claim 9 wherein the 1,1,1,3,3-pentachloropropane and the hydrogen fluoride are introduced continuously or intermittently to the Step (A), and the reaction product gas and the reaction fluid are recovered continuously or intermittently.

11. The production method according to claim 7 wherein each of the plurality of intermediate products is selected from the group consisting of 1,1,3,3-tetrachloro-1-fluoropropane (241fa), 1,1,1,3-tetrachloro-3-fluoropropane (241fb), 1,3,3-trichloro-3-fluoropropene (1231zd), 1,3,3-trichloro-1-fluoropropene (1231zb), 3,3,3-trichloro-1-fluoropropene (1231ze), 1,1,3-trichloro-3-fluoropropene (1231za), 1,3,3-trichloro-1,1-difluoropropane (242fa), 1,1,3-trichloro-1,3-difluoropropane (242fb), 1,3-dichloro-3,3-difluoropropene (1232zd), 3,3-dichloro-1,3-difluoropropene (1232ze), 3,3-dichloro-1,1-difluoropropene (1232zc), 1,3-dichloro-1,3-difluoropropene (1232zb), cis-1-chloro-3,3,3-trifluoropropene (1233zd(Z)), 3,3-dichloro-1,1,1-trifluoropropane (243fa), 1,3-dichloro-1,1,3-trifluoropropane (243fb), 1,1-dichloro-1,3,3-trifluoropropane (243fc), 1-chloro-1,1,3,3-tetrafluoropropane (244fb) and 3-chloro-1,1,1,3-tetrafluoropropane (244fa).

12. The production method according to claim 7 wherein at least one of the plurality of intermediate products comprises 1,3,3-trichloro-1,1-difluoropropane (242fa).

13. The production method according to claim 7 wherein the reaction temperature of the Step (B) is from 150° C. to 500° C.

14. The production method according to claim 7 wherein unreacted intermediate products are recovered and employed in the Step (B).

15. The production method according to claim 7 wherein cis-1-chloro-3,3,3-trifluoropropene is obtained in the Step (B) together with trans-1-chloro-3,3,3-trifluoropropene.

16. The production method according to claim 15 wherein cis-1-chloro-3,3,3-trifluoropropene obtained is subjected as intermediate products to the Step (B).

17. The production method according to claim 15 wherein cis-1-chloro-3,3,3-trifluoropropene obtained is heated at a temperature from 150° C. to 600° C. to obtain trans-1-chloro-3,3,3-trifluoropropene.

18. The production method according to claim 2 wherein the hydrocarbon compound having 3 carbon atoms is at least one selected from the group consisting of 1,1,1,3,3-pentafluoropropane (245fa), trans-1,3,3,3-tetrafluoropropene (1234ze(E)), cis-1,3,3,3-tetrafluoropropene (1234ze(Z)), 1,1,3,3-tetrafluoropropene (1234zc), and 3,3,3-trifluoropropine.

19. The production method according to claim 6 wherein the hydrocarbon compound having 3 carbon atoms is at least one selected from the group consisting of 1,1,1,3,3-pentafluoropropane (245fa), trans-1,3,3,3-tetrafluoropropene (1234ze(E)), cis-1,3,3,3-tetrafluoropropene (1234ze(Z)), 1,1,3,3-tetrafluoropropene (1234zc), and 3,3,3-trifluoropropine.

20. The production method according to claim 8 wherein the hydrocarbon compound having 3 carbon atoms is at least one selected from the group consisting of 1,1,1,3,3-pentafluoropropane (245fa), trans-1,3,3,3-tetrafluoropropene (1234ze(E)), cis-1,3,3,3-tetrafluoropropene (1234ze(Z)), 1,1,3,3-tetrafluoropropene (1234zc), and 3,3,3-trifluoropropine.

* * * * *